(12) United States Patent
Zofchak et al.

(10) Patent No.: US 6,723,310 B2
(45) Date of Patent: Apr. 20, 2004

(54) HAIR CONDITIONING FORMULATION

(76) Inventors: Albert Zofchak, 6 Gulfstream Blvd., Matawan, NJ (US) 07747; John C. Carson, 2310 West St., Union City, NJ (US) 07087

( * ) Notice: Subject to any disclaimer, the term of this patent is extended or adjusted under 35 U.S.C. 154(b) by 0 days.

(21) Appl. No.: 10/207,635

(22) Filed: Jul. 29, 2002

(65) Prior Publication Data

US 2004/0018164 A1 Jan. 29, 2004

(51) Int. Cl.[7] .......................... A61K 7/075; A61K 7/08
(52) U.S. Cl. ................ 424/70.1; 424/70.13; 424/70.21; 424/70.27
(58) Field of Search ................ 424/70.13, 70.27, 424/70.21, 70.1

(56) References Cited

U.S. PATENT DOCUMENTS

| 4,548,810 A | 10/1985 | Zofchak |
| 6,258,348 B1 | 7/2001 | Tsivkin |

*Primary Examiner*—Jyothsna Venkat
(74) *Attorney, Agent, or Firm*—Henry D. Coleman; R. Neil Sudol; William J. Sapone

(57) ABSTRACT

The invention provides a hair conditioning formulation useful in repairing split ends comprising: (a) an amphoteric or cationic guar gum; and (b) a Necon fatty dialkyl amine salt, wherein the formulation contains natural or synthetic gums.

7 Claims, 11 Drawing Sheets

FIG. 3
NECON CPS
PEG-15 COCAMINE PHOSPHATE / OLEATE COMPLEX
1st Step:
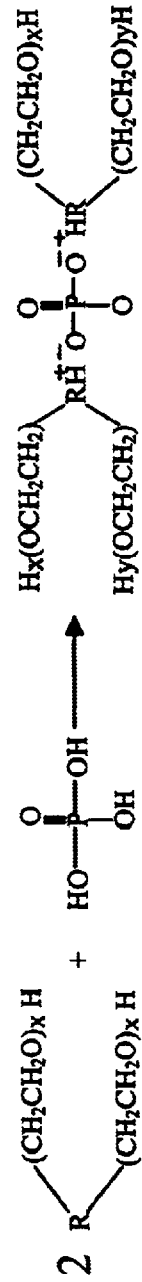
2 PEG 15 COCAMINE + PHOSPHORIC ACID → PEG 15 COCAIME PHOSPHATE
CAS # 8051-52-3
X + Y = 15 Mol (EO) Avg.
2nd Step:
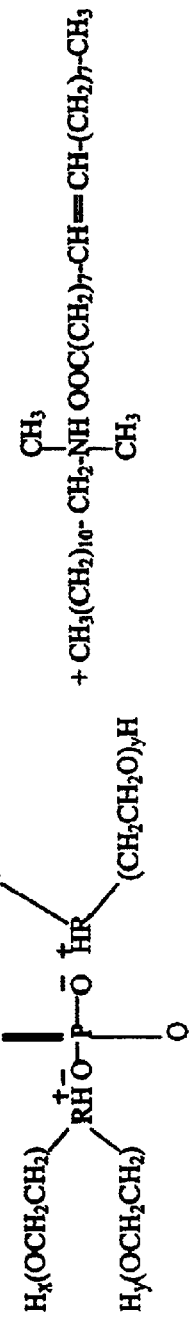
5 PEG 15 COCAMINE PHOSPHATE + $CH_3(CH_2)_{10}$—$CH_2$—NH OOC$(CH_2)_7$—CH=CH—$(CH_2)_7$—$CH_3$ (with two $CH_3$ groups on N) → NECON CPS
1 NECON LO (DIMENTHYL LAURAMINE OLEATE)

NECON DLD
BIS (DIMETHYL LAURAMINE) DIMER DILINOLEATE
CAS # 125804-09-3

FIG. 5
NECON CPS
PEG-15 COCAMINE PHOSPHATE / OLEATE COMPLEX
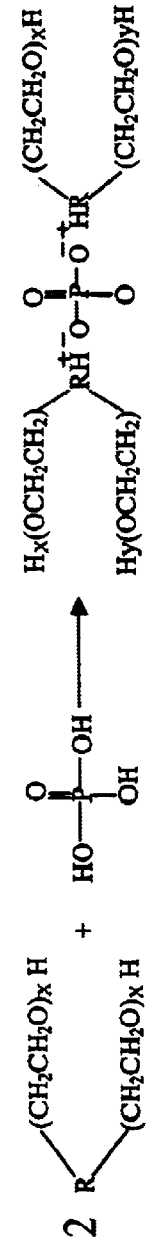
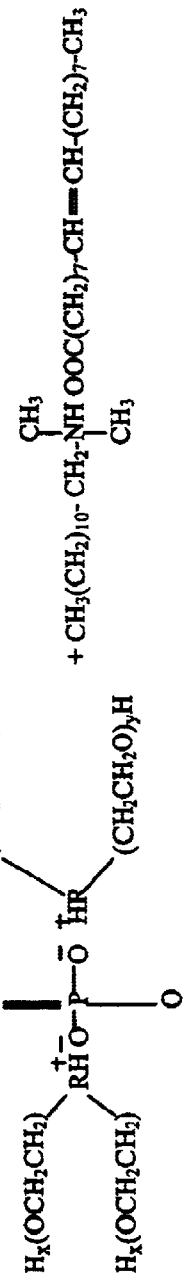

NECON SOLC

INCI NAME: LINOLEAMIDOPROPYL DIMETHYLAMINE LACTATE

FIG. 8 NECON BAB

NECON LO

INCI NAME: DIMETHYL LAURAMINE OLEATE

CAS # 70321-83-4

DIMETHYL LAURAMINE
CAS # 112-18-5

OLEIC ACID
CAS # 112-80-1

N,N – DIMETHYL-1-DODECAAMINE-9-OCTADECENOATE
CAS # 70321-83-4

FIG. 10
NECON BD
INCI NAME: DI BEHENAMIDOPROPYL DIMETHYLAMINE DILINOLEATE
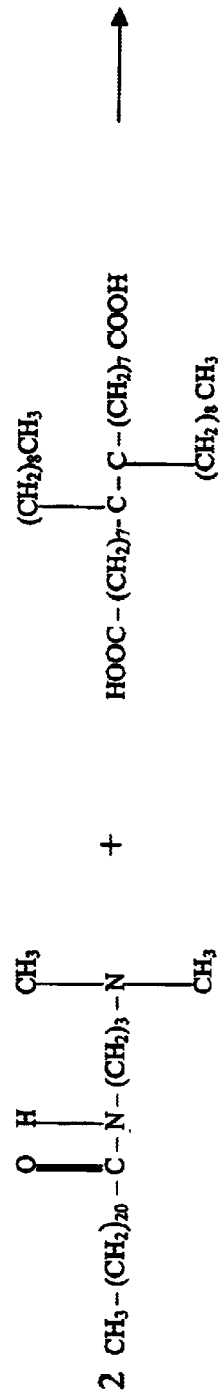
BEHENAMIDOPROPYL DIMETHYLAMINE
CAS # 60270-33-9
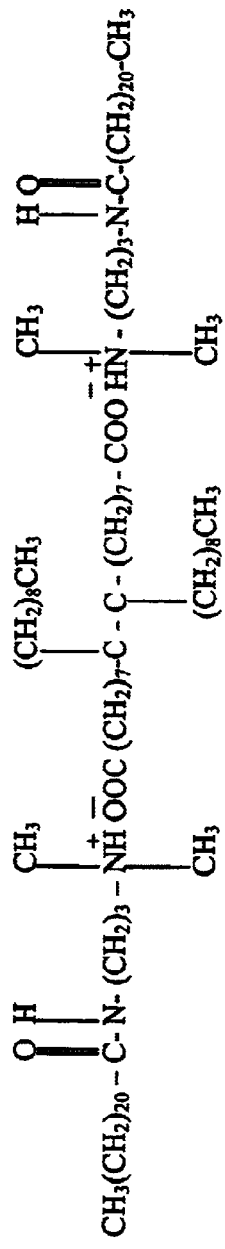
DILINOLEIC ACID
CAS # 6144-28-1
BIS (DOCOSAMIDOPROPYL DIMETHYAMINE) DILINOLEATE

NECON LO-80

INCI NAME: LINOLEAMIDOPROPYL DIMETHYLAMINE DIMER DILINOLEATE
CAS # 125804-10-6

HAIR CONDITIONING FORMULATION

BACKGROUND OF THE INVENTION

Hair is a keratinous substance, which is constantly subjected to environmental stresses such as low humidity, UV radiation, contact with surfactants, and physical abrasion, and also to internal stresses which are a consequence of the natural aging process. Because of these stresses, hair looses its natural conditioning and moisturizing components and often appears rough, dry, and damaged. Thoroughly cleansed hair is extremely difficult to comb, in either the wet or the dry state, because the individual hair fibers tend to snarl, kink and interlock with each other. In addition, incompletely dried hair, such as hair dried with towel, has poor brushing properties, and after complete drying, the hair does not set well. Furthermore, the combing or brushing property of the hair remains poor, and the hair has undesirable electrostatic properties in a low humidity atmosphere that causes the hair to "fly away", thereby further reducing the brushing properties of the hair. The unsatisfactory combing or brushing property of hair immediately after shampooing also causes hair damage, such as split ends or hair breakage.

"Split ends" refers to a condition wherein the ends of the hair are split into two or more shafts, resulting in a frizzy appearance. Numerous conditioner and shampoo formulations have been developed in an effort to ameliorate split ends. The majority of these seek to prevent split end damage as opposed to repairing split ends. Known compositions that do seek to repair split ends include those disclosed in U.S. Pat. No. 6,258,348 B1 ("'348 Patent"), the complete disclosure of which is hereby incorporated by reference. The compositions disclosed in the '348 Patent as being useful in split-end repair comprise three polymers: guar, a betaine-based polyurethane surfactant, and a silicone polyurethane. In particular, the '348 Patent discloses that formulations comprising amphoteric or cationic guar (e.g., guar hydroxypropyl trimonium chloride, CTFA nomenclature), in combination with polymeric adhesive agents comprising a betaine based polyurethane surfactant and a silicone polyurethane, can repair a substantial percentage of various split end test samples. According to the disclosure of the '348 Patent, the amphoteric or cationic guar gums do not achieve substantial split end repair in the absence of the other disclosed polymeric substituents.

U.S. Pat. No. 4,548,810 ("'810 Patent"), the complete disclosure of which is hereby incorporated by reference, discloses fatty dimethyl amine salts, which are known generally by the trade name "Necon" (Necon™) and which are available commercially from Alzo International, Inc., Sayreville, N.J. In particular, the Necons are long chain tertiary amine salts of fatty acids ranging from $C_6$ through $C_{36}$ and have been used in skin and hair contacting formulations in such applications as shaving creams, skin creams, lotions, bar soaps, liquid soaps, body oils, hair colorants, afterbath lotions and splashes, lipsticks, lip balms, bath products and sunscreen formulations for their attributes of assisting in the solubilization of components in these formulations and their conditioning characteristics of the skin and hair.

As disclosed in the '810 Patent, the Necons are non-adhesive compositions which increase the slip and lubricity of hair, and as such they would not be expected to contribute to split end repair if included in a hair conditioning formulation. This is because, unlike the polyurethane surfactant and silicone polyurethane components described in the '348 Patent, the Necons would not be expected to deposit on a hair surface in a manner thought necessary to repair split ends. As is the case with other agents traditionally used to increase the slip and lubricity of hair such as stearalkonium chloride, the presence of a Necon alone in a hair conditioning formulation does not appear to contribute to the repair of split ends.

There has been no suggestion that a Necon could be substituted in guar gum-containing hair conditioning formulations for other non-guar polymeric constituents, such as the betaine-based polyurethane surfactant or silicone polyurethane described in the '348 Patent, to make a formulation which achieves substantial split end repair.

SUMMARY OF THE INVENTION

The present invention provides a hair conditioning formulation useful in repairing split ends comprising: (a) an amphoteric or cationic guar gum, preferably a cationic guar gum, even more preferably a quaternary ammonium derivative hydroxypropylguar; and (b) a fatty dialkyl (preferably, dimethyl) amine salt (Necon) as otherwise described herein, wherein the formulation may contain a natural or synthetic gum.

In a preferred embodiment, the formulation of the instant invention is a shampoo comprised of an amphoteric or cationic guar gum and one or more fatty dimethylamine salts selected from the group consisting of:

polyethyleneoxide 15-cocamine phosphate/oleate complex (Necon™ CPS-65), lauryldimethylamine lactate (Necon™ LL), lauryldimethylamine oleate (Necon™ LO), lauryldimethylamine dimer dilinoleate (Necon™ DLD), linoleamidopropyldimethylamine lactate (Necon™ SOLC), behenamidopropyldimethylamine behenate (Necon™ BAB), behenamidopropyldimethylamine dimer dilinoleate (Necon™ BD), and linoleamidopropyldimethylamine dimer dilinoleate (Necon™ LO-80). All of the above Necon products are available commercially from Alzo International, Inc., Sayreville, N.J.

BRIEF DESCRIPTION OF THE DRAWINGS

FIGS. 3 through 11 illustrate the fatty dimethylamine salts described above.

BRIEF DESCRIPTION OF THE INVENTION

Figure 1:
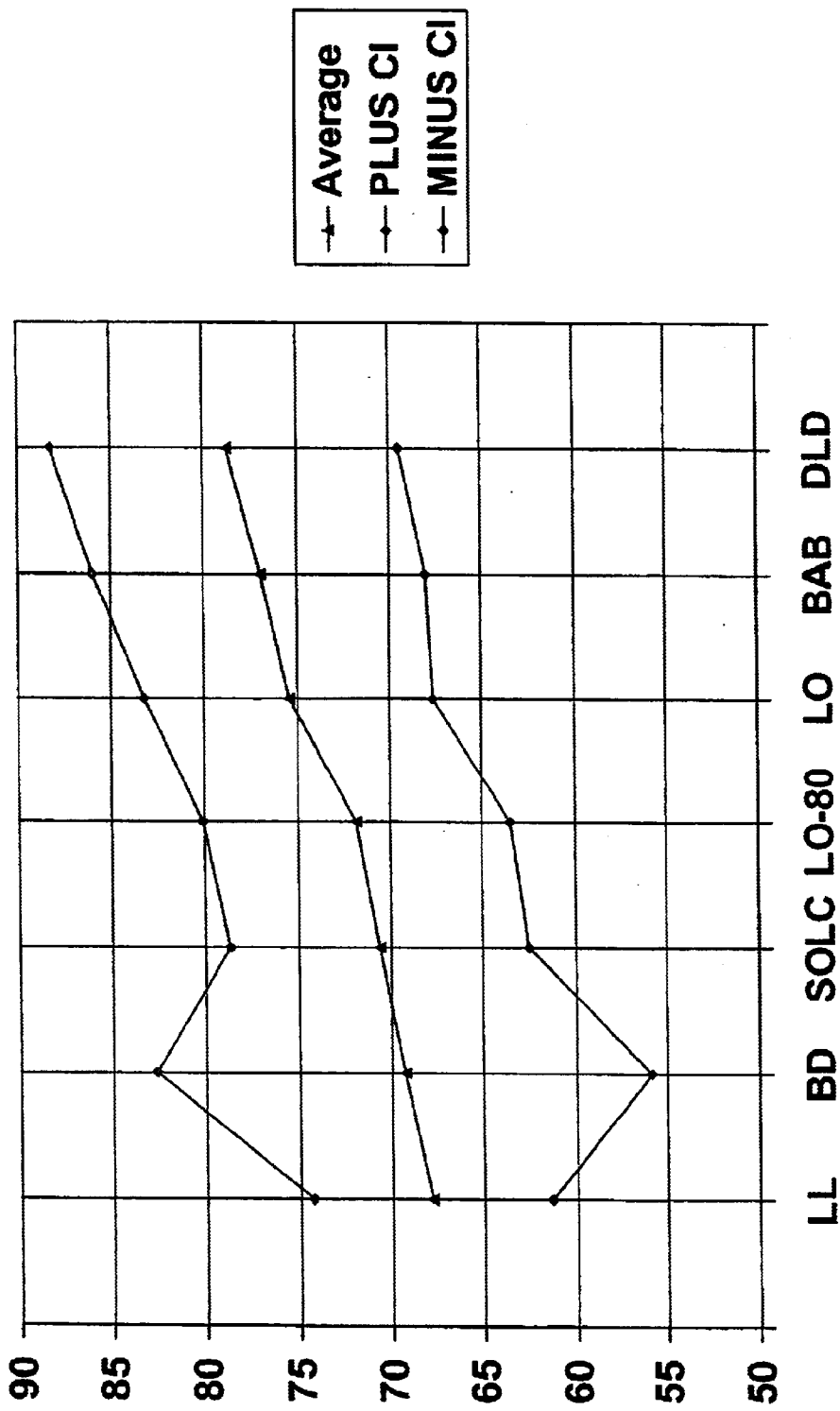
FIG. 1 illustrates the percentage of human hair split end repair achieved using various formulations of the instant invention.

Fatty dimethylamine salts (Necons) used in the present invention may be described according to the following chemical formula:

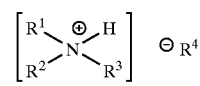

where $R^1$ is a $C_8$ to $C_{40}$ preferably a $C_{12}$ to $C_{36}$) straight or branch-chained, saturated or unsaturated hydrocarbon group (preferably a saturated or alkyl group) or a fatty amido group according to the formula:

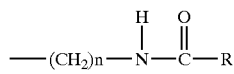

where R is a $C_8$ to $C_{40}$ (preferably a $C_{12}$ to $C_{36}$, even more preferably a $C_{12}$ to $C_{22}$) straight or branch-chained, saturated or unsaturated hydrocarbon group (preferably a saturated or alkyl group), n is from 1 to 5, preferably 2 or 3, more preferably 3 (propylene group); $R^2$ and $R^3$ are methyl, ethyl or propyl groups, preferably methyl groups; and $R^4$ is a $C_2$ to $C_{40}$ (preferably a $C_3$ to $C_{36}$) acid anionic residue or diacid dianionic (both carboxylic acid residues are ionized as carboxylate anions) residue (obtained from neutralization of a dibasic acid), including a dimer acid dianionic residue, preferably, an isostearic acid anionic residue, a ricinoleic acid anionic residue, a hydroxystearic acid anionic residue, more preferably, a lactic acid anionic residue, an oleic acid anionic residue, a behenic acid anionic residue or a dimer-dilinoleic acid dianionic residue, among others.

It will be understood when the term "anionic residue" is used, the term signifies the radical is such that when the radical is combined with a (−) charge, the radical and (−) charge form the corresponding anion.

Guar gums which may be used in the formulation of the instant invention are amphoteric guar gums or cationic derivatives of guar gum or locust bean gum as disclosed in the '348 patent, as well as U.S. Pat. Nos. 4,557,928 and 4,387,090, relevant portions of which are incorporated by reference herein. Guar gum is obtained from the endosperm from *Cyamopsis tetragonolobus* and is made up of straight chain mannan grouping with relatively regular branching on every second mannose by a single galacotose unit. Guar gums useful in the present invention as described in the '348, '928 and '090 patents preferably having substitutions on the galactose unit of the polymer. Preferred cationic guar gums are obtained by reacting reactive quaternary ammonium compounds with hydroxyl groups on the galactose sugars of guar to obtain the corresponding cationic derivative. Preferably, the cationic guar gum utilized is a quaternary ammonium derivative of hydroxypropylguar, for example guar hydroxypropyltrimonium chloride (known in the trade as Jaguar C-13S) or a relative cationic guar gum carboxymethyl guar hydroxypropyltrimonium chloride, available from National Starch and Chemical Company. Another preferred cationic guar gum is 3-(trimethyamino)-2-hydroxypropylguar chloride according to the chemical structure:

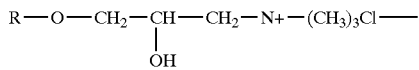

Where R is the polygactomannan molecule of guar and is sold as Cosmedia Guar 216N by Henkel Corporation.

Cellulosic-based cationic guar gums such as Poymer JR and Quatrisoft (both manufactured by Dow chemical) may also be used. Preferred formulations of the instant invention include, on a weight percentage basis, from about 0.05% to about 10%, more preferably about 0.1% to about 5% by weight in total of one or more of the aforementioned amphoteric or cationic guar gum derivatives.

Preferred formulations of the instant invention also include, on a weight percentage basis, from about 0.05% to about 10% by weight, more preferably about 0.1% to about 5% by weight of fatty dimethylamine salt (Necon).

Such Necons include:
polyethyleneoxide 15-cocamine phosphate/oleate complex (Necon CPS-65),
lauryldimethylamine lactate (Necon LL),
lauryldimethylamine oleate (Necon LO),
lauryldimethylamine dimer dilinoleate (Necon DLD),
linoleamidopropyldimethylamine lactate (Necon SOLC),
behenamidopropyldimethylamine behenate (Necon BAB), behenamidopropyldimethylamine dimer dilinoleate (Necon BD), and
linoleamidopropyldimethylamine dimer dilinoleate (Necon LO-80).

The '810 Patent discloses how to make Necons useful in the formulations of the instant invention. Such methods, where relevant, are incorporated by method herein.

An especially preferred formulation of the instant invention comprises, on a weight percentage basis, around 0.25% of a cationic guar gum such as guar hydroxypropyl trimonium chloride (Jaguar CS-13) and around 2% to 3% of lauryldimethylamine dimer dilinoleate (Necon DLD). Formulation 65G of Example 3, Table 5, herein reflects preferred Necon and guar gum types and amounts useful in a shampoo formulation made in accordance with the instant invention.

A relationship between the composition of certain Necons and their relative efficacy in repairing split ends has been discovered. As detailed in Example 3 herein, experiments using shampoo formulations made in accordance with the instant invention indicate that Necons made with monofunctional amines and acids are increasingly effective at split end repair as they become increasingly hydrophobic, whereas Necons that are made from dimer acids become more effective at repairing split ends as they become more hydrophilic. A schematic depicting the observed relationship between Necon composition and split end repair efficacy is set forth in FIG. 2 and may be summarized as follows.

Necons LL, LO, and DLD are lauryl dimethylamine based salts; the lactate salt (LL) is the most hydrophilic of the three, the oleate salt (LO) is less hydrophilic than LL but more so than DLD, and the dimer acid salt (DLD) is the least hydrophilic of the three. Formulations containing Necon LL, while useful in repairing split ends, did not repair split ends as well as Necon LO. In turn, Necon LO did not perform as well as Necon DLD (relationship (2) in FIG. 2). Thus, in the case of Necons which are lauryl dimethylamines, split end repair efficacy is inversely proportional to hydrophilicity. This relationship is supported by the observation that use of Necon SOLC (linoleamidopropyldimethylamine lactate) in shampoo formulations of the instant invention results in less split end repair than the use of Necon DLD (lauryldimethylamine dimer dilinoleate), but results in more split end repair than the use of the more hydrophilic Necon LL (lauryldimethylamine lactate).

Figure 2:
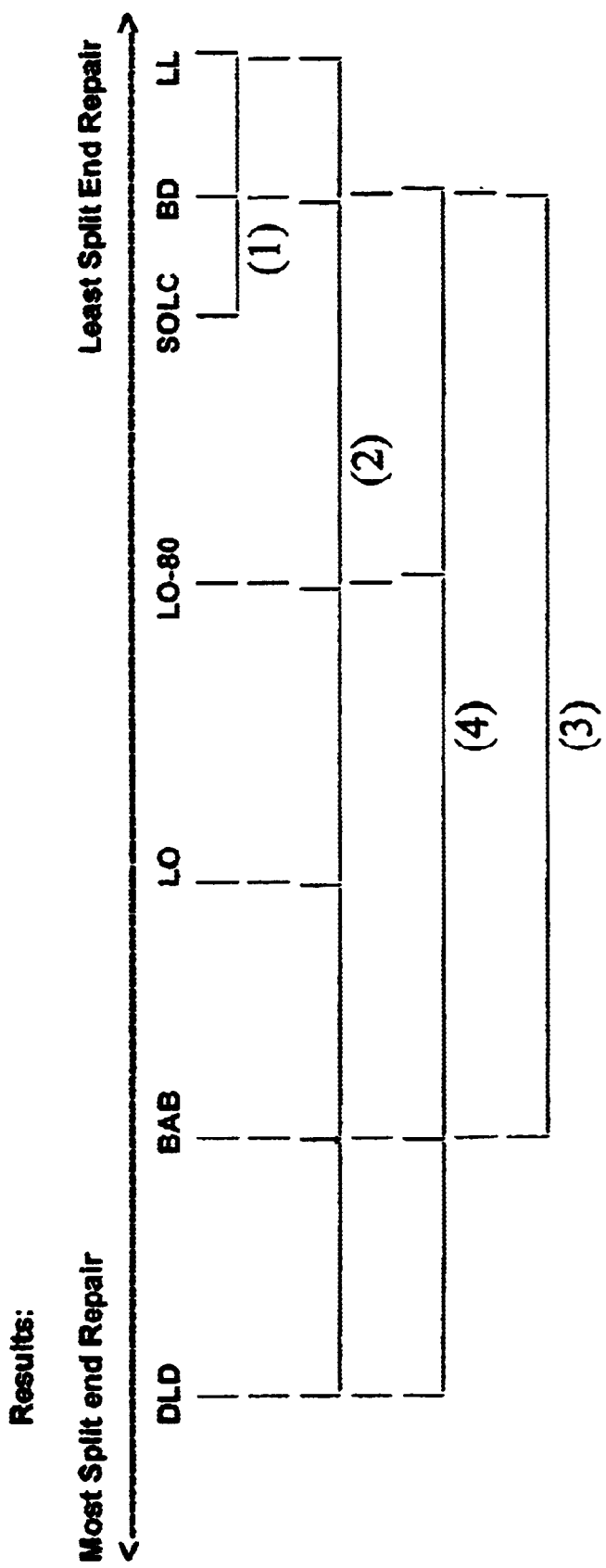
FIG. 2 illustrates a schematic representation of the relative efficacy in split end repair of various types of Necons useful in formulations of the instant invention.
Figure 4:
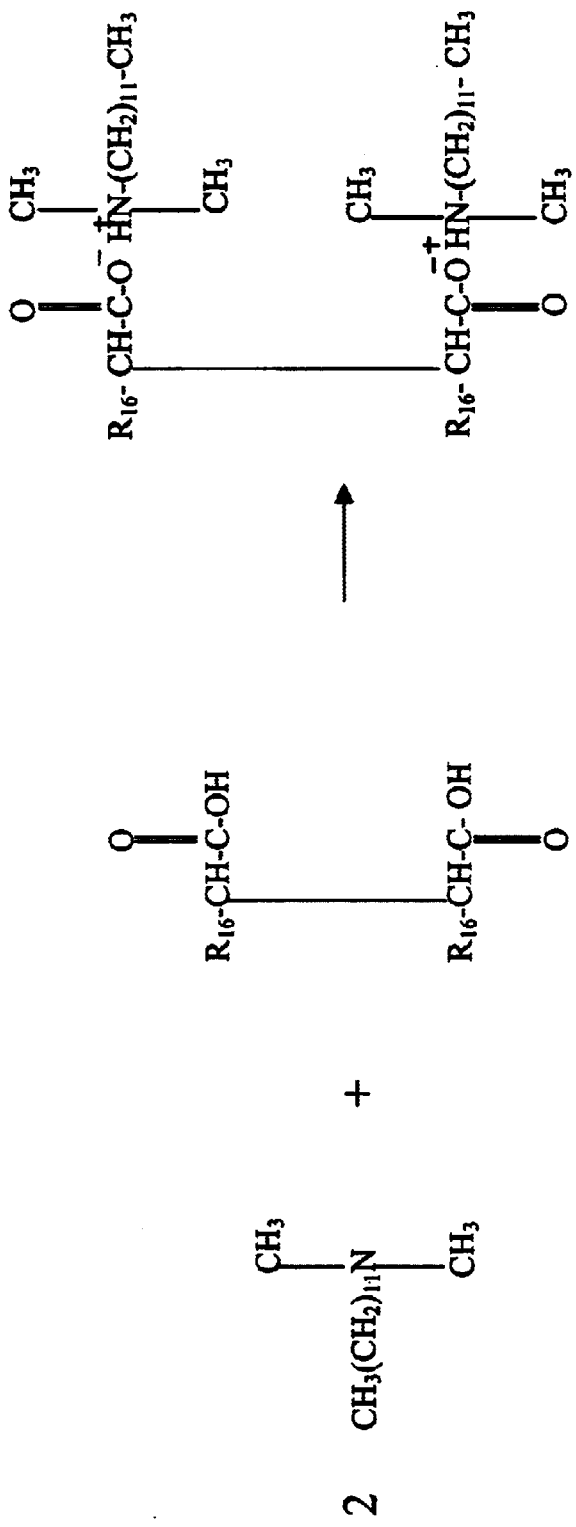
Figure 6:
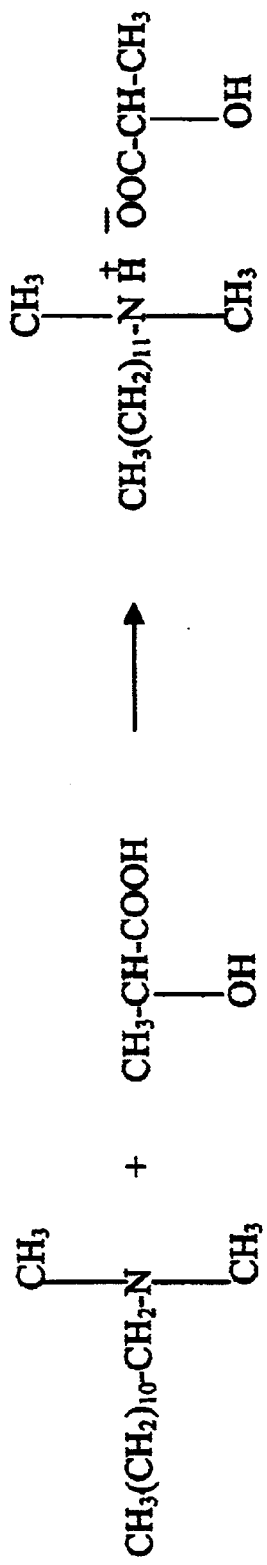
Figure 7:
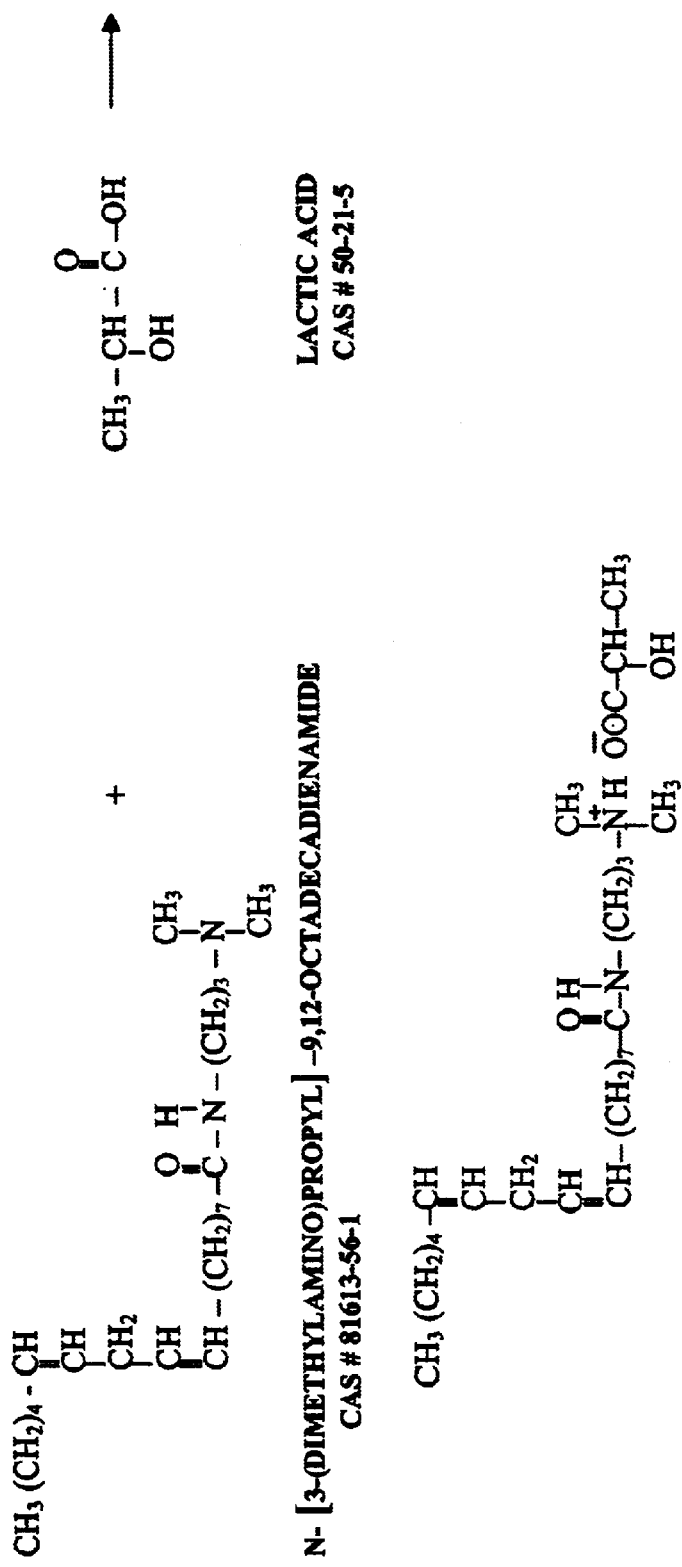
Figure 8:
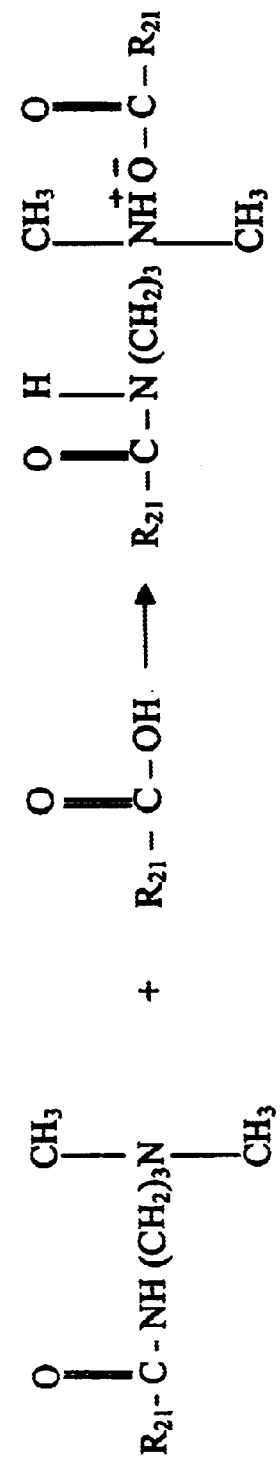
Figure 9:
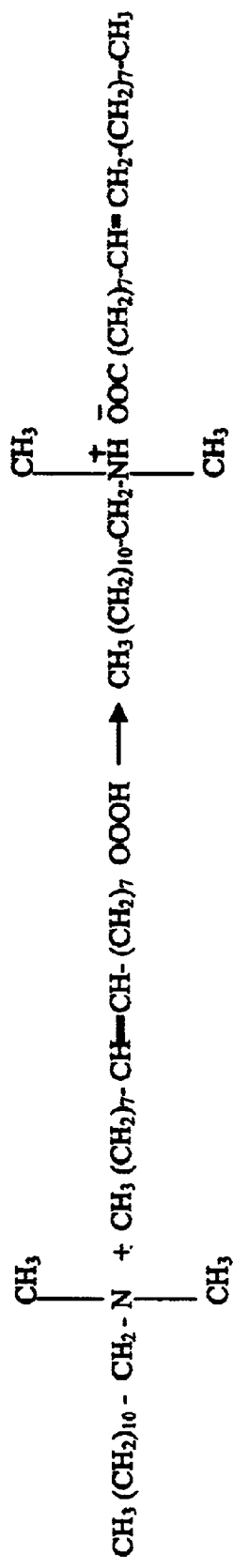
Figure 11:
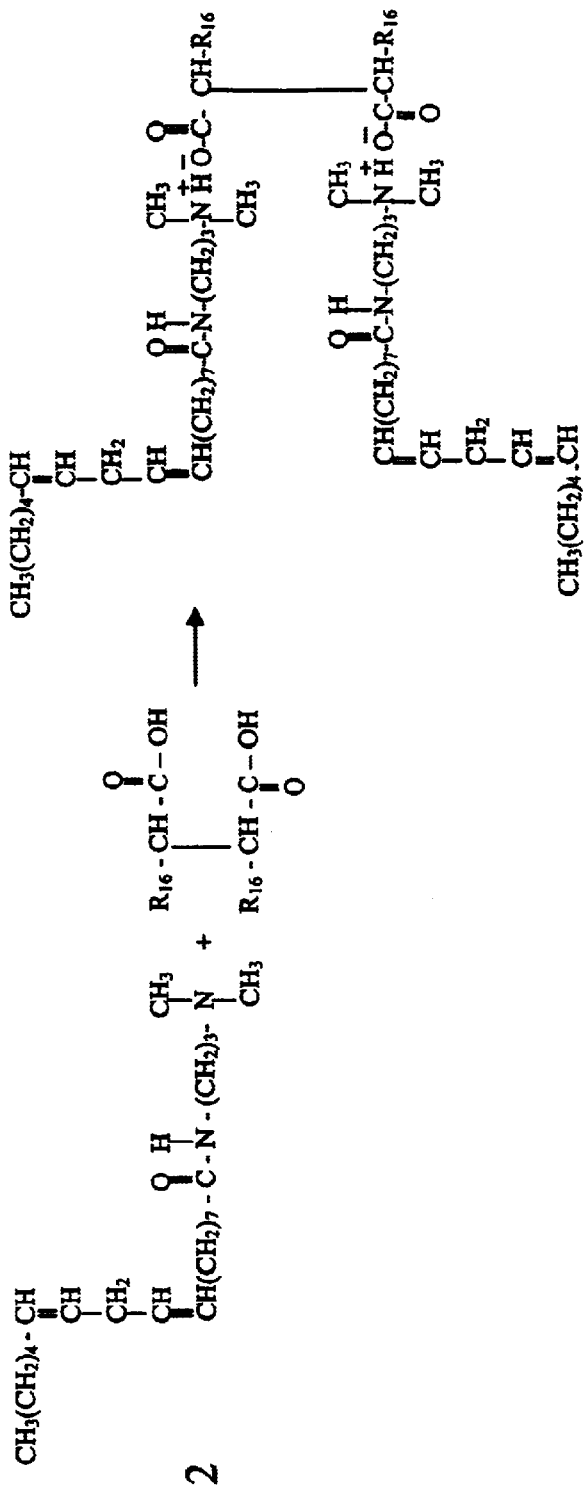

Necon BAB (behenamidopropyldimethylamine behenate) repairs split ends better than the more hydrophilic Necon BD (relationship (3) in FIG. 2). (Necon BAB is believed to be less hydrophilic than Necon BD because it forms an opaque solution in shampoo while Necon BD forms a clear solution.) Thus, decreasing the hydrophilicity of the Necon improves the repair of split ends irrespective of whether the amine or the acid portion of the Necon is changed to decrease the hydrophilicity. However, where a dimer acid is used as the anion in the Necon, hydrophilicity of the salts is directly proportional to split end repair (relationship (4) in FIG. 2). Necon DLD was more effective than Necon LO-80 (linoleamidopropyldimethylamine dimer dilinoleate) in repairing split ends, and Necon LO-80 in turn was more effective than Necon BD.

Formulations of the instant invention include solutions, emulsion (e.g., creams), gels, rinses, or shampoos. When the formulation of the instant invention is in the form of a shampoo, it provides desirable cleansing, foaming, detangling and conditioning properties and also repairs split ends. Formulations of the instant invention usually include water in an amount of 20% to 90% on a weight percentage basis. Preferred formulations in the form of a shampoo comprise about 30% to about 60%, more preferably about 40% to 50% water on a weight percentage basis.

Surfactants that function as detergents to clean the hair can also be used in the formulations of the instant invention. Conventional surfactants such as anionic, cationic and amphoteric surfactants can be used; suitable surfactants include those disclosed in the '348 Patent. In shampoo formulations of the instant invention, sodium-based surfactants are preferred over ammonium-based surfactants. Commercial sources of such surfactants can be found in McCutcheon's EMULSIFIERS AND DETERGENTS, North American Edition, 1984, McCutcheon Division, MC Publishing Company, the complete disclosure of which is hereby incorporated by reference. The amount of surfactant can range from about 1% to about 70% on a weight percentage basis, more typically from about 2% to about 50%. Preferred surfactants include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, sodium dodecyl benzene sulfonate, and cocoamphocarboxyglycinate. Ammonium laureth sulfate and sodium laureth sulfate are particularly preferred.

Formulations of the instant invention may include auxiliary conditioning agents such as quaternary ammonium compounds, amines, ethyl sulfates (non-quats) and other cationic polymers. Preferred auxiliary conditioning agents include polyquaternium 10 or benhentrimonium methosulfate. Such auxiliary conditioning agents can be used in an amount of from about 0.1% to about 3.0% on a weight percentage basis, preferably from about 0.5% to about 2.0%.

One or more emollients and humectants are generally employed in formulations of the instant invention. Examples of suitable emollients include, but are not limited to, mineral oil and petrolatum. Other emollients may include cetyl or stearyl alcohol, paraffin or lanolin alcohol. Emollients are generally employed in the formulations of the instant invention in a weight percentage range of from about 1% to about 20%, preferably from about 2.0% to about 10%. Examples of suitable humectants include, but are not limited to, propylene glycol, butylene glycol, hexylene glycol, glycerin and sorbitol. As a general guide, humectants are used in a weight percentage range of from about 1% to about 20%, preferably from about 2% to about 5%.

One or more emulsifying agents are also typically used in formulations of the instant invention. Emulsifiers typically provide dispersion and suspension of the components, and render a creamy and lubricous consistency to the composition. Nonlimiting examples of emulsifying agents suitable for use include alkoxylated alcohols and fatty alcohols, such as stearyl, cetyl and cetearyl alcohols, ethoxylated sorbitan esters, ethoxylated lanolin and derivatives thereof. As a general guide, emulsifiers can be used in amounts of about 0.5% to about 16% on a weight percentage basis, preferably from about 1–2% to about 12%, and more preferably from about 3% to about 8%.

Opacifying agents are conventionally used in cream compositions. Suitable opacifying agents include the higher alcohols, such as stearyl, cetyl and behenyl alcohol, and the higher acids, such as behenic acid, although such acids are not used in shampoos, but rather other compositions including conditioning compositions according to the present invention. Sodium chloride and sodium sulfate can also be used as opacifying aids. Care should be used to limit the concentration of these salts in certain instances where gellation occurs. Alkaline earth metal fatty acid soaps, such as calcium stearate and magnesium stearate, are also suitable. Care must be taken to avoid defoaming in shampoo compositions. Magnesium silicates are also useful for this purpose. Opacifying agents, such as EGMS, EGDS, lytron, polectron, GMS and GDS, among other commonly used components of shampoos and/or conditioners, are typically present in an amount ranging from about 0.1% to about 10% on a weight percentage basis, preferably from about 0.5% to about 5%.

Thickening agents increase the viscosity of a hair-related product. Suitable materials are natural gums such as tragacanth, xanthan, acacia and locust bean; and synthetic gums such as hydroxypropylcellulose, hydroxypropylmethylcellulose and hydroxyethylcellulose. Polyvinyl alcohols can also be used. Alkanolamides, "super" amides and polyethoxylated glycol, glycerol and penterythryl stearates may also be used. Thickening agents are used in formulations of the instant invention in an amount needed to provide the desired viscosity. Amounts typically employed are from about 0.1% to a bout 10% on a weight percentage basis, preferably, from about 0.5% to about 5%. The final viscosity of the product should be such that it can be applied and dispersed throughout the hair without dripping.

Other optional additives can include foam stabilizers, viscosity builders, preservatives, sequestrants, antioxidants such as sodium sulfite, BHT or vitamin E, chelating agents such as EDTA, suspending agents, fragrances or perfumes, proteins and protein hydrolysates, herbal components and botanical extracts, sunscreens, and pH control agents such as citric acid. These additives are usually present in an amount of less than 5% on a weight percentage basis. An antidandruff component, e.g., selenium sulfide or zinc omadine, among others, may also be included at an effective level.

A preferred shampoo formulation made in accordance with the instant invention comprises a surfactant blend including, e.g., the anionic surfactant sodium N-cocoyl 1-glutamate, a microbial preservative, around 0.25% by weight of a Jaguar brand cationic guar gum, around 2.0% by weight of a Necon selected from the group consisting of Necon LO80, Necon LL, Necon DLD, Necon BAB, Necon LO, Necon CPS-65, Necon BD and Necon SOLC, and water. While not essential for split-end repair, thickeners, fragrances, solubilizers, and chelating agents, together with other components listed above (e.g., opacifying agents or emilsifiers) can also be added to these formulations. As illustrated in the experimental results set forth hereinafter in Examples 2 and 3, and as illustrated in FIGS. 1 and 2, all of the Necons tested proved useful in making formulations of the invention which repaired split ends, but some Necons performed better in this regard than others.

The following examples illustrate these and other embodiments of the instant invention and should not be construed as limiting in any regard.

EXAMPLES

Example 1

Shampoo Formulations: Relative Effectiveness of Non-Necon Formulations

Materials and Methods

In this Example, and the following Examples 2 and 3, shampoo split end repair was measured using the following hair sample protocol.

Individual hairs having a split terminal end were selected from bulk bundles of "hair with split ends" that is commercially available form International Hair Importers of Bellrose, N.Y. Specifically, this hair is a 7 inch long, european, dark brown hair that contains a relatively high percentage of split end damaged fibers. For selection, the hair bundles were viewed under a magnifying lens and individual hair fibers with a split terminal end were removed from the bundle. The selection criterion used was that the length of the terminal split should be from about 1 mm to about 5 mm in length. About twenty such selected hairs were formed into tresses using crimp-on electrical ring terminals. Following crimping, the hair fibers were cemented in the ring terminal with cyanoacrylate glue. The glue was allowed to set for at least 24 hours after which the tresses were cleaned by agitating them (up and down) in a solution composed of 30% Isopropyl Alcohol, 30% Sodium Laureth (2) Sulfate and 40% Deionized Water. The tresses were then rinsed under running tap water @ 40° C. for 1 minute. After drying for at least 24 hours at room temperature, one of these small split end tresses was added (in such a manner so as to be removeable for evaluation) to a larger, shampoo cleaned, 2 gram hair tress composed of 7 inch long, virgin, european, dark brown hair.

In this example, and the following Examples 2 and 3, Steol CS 230 and WAC are surfactants available from Stepan and Foamtaine CAB (an alkyl betaine surfactant available from Alzo) is a surfactant SOURCE/TYPE, Ajinomoto CS-22 is an anionic acyl glutamate surfactant, available from Ajinomoto Company, and Phenobact is an anti-microbial preservative. The guar gum used was Jaguar C13S, a cationic guar gum commercially available from Rhodia. It is chemically known according to its CTFA designation: guarhydroxypropyltrimonium chloride, a quaternary ammonium derivative of hydroxypropyl guar.

Preparation of Control Sample

Sample 6 from Example 3, Table 4 of the '348 Patent (which is disclosed to have achieved 80% split end repair) was prepared with the following variations:

(1) as the individual amounts of Sodium Lauryl Sulfate, Sodium Laureth Sulfate and Cocamidopropyl betaine are not specified in the patent, and only the total amount of a "Surfactant Blend" comprising these surfactants is disclosed (45%), 15% of each surfactant was used as an approximation;
(2) Cocamide MEA was not used;
(3) Crovol A-70 (PEG-60 Almond Glycerides) was omitted;
(4) the antimicrobial preservative used was Phenobact, not Kathon CG and the amount of preservative was increased from 0.03% to 1.00%;
(5) a different fragrance was used and the level was reduced from 0.75% to 0.50%;
(6) the amount of Citric acid was increased from 0.0025% to 0.01%; and
(7) the amount of Tetrasodium EDTA was reduced from 0.012% to 0.01%.

The changes noted in items 2 through 7 were made either because: (1) the raw material was not available and therefore deleted (items 2 and 3); (2) the raw material was not available, but a substitute that was believed to be suitable was available (items 4 and 5); or (3); or the exact amount of the chemical added was not judged to be critical to the split end repair function of the shampoo (items 6 and 7).

In order to determine that the changes listed did not compromise the ability of the shampoo to mend split ends, and in order to determine the effect of surfactant sodium and ammonium cations, Formulations 1 and 2 (Table 1) were prepared and tested for split end repair.

TABLE 1

| Ingredients | 1 % | 2 % |
|---|---|---|
| Phase A | | |
| Stepanol WAC | 15.00 | — |
| Steol CS-230 | 15.00 | — |
| Stepanol AM | — | 15.00 |
| Steol CA-230 | — | 15.00 |
| Foamtaine CABG (35) | 15.00 | 15.00 |
| Acyl Glutamate CS-22 | 7.00 | 7.00 |
| Polyderm PPI-Si WS | 1.00 | 1.00 |
| Foamtaine PPI-RC | 3.00 | 3.00 |
| Phenobact | 1.00 | 1.00 |
| Crothix Liquid | 0.75 | 0.75 |
| Fragrance | 0.50 | 0.50 |
| Phase B | | |
| Deionized Water | 41.48 | 41.48 |
| Jaguar C-13S | 0.25 | 0.25 |
| Phase C | | |
| Citric Acid | 0.01 | 0.01 |
| Tetra Sodium EDTA | 0.01 | 0.01 |
| | 100.00 | 100.00 |

Two hair tresses, as previously described, were assigned to each of Formulations 1 and 2. Each tress was wetted in running 40° C. tap water for 15 seconds, immediately shampooed with 1 cc of the shampoo for one minute and rinsed under running 40° C. tap water for one minute. This process was repeated once. The split end tress was then removed from the 2 gram tress and hung to air dry overnight. A magnifying lens was used to count the number of split ends remaining in each tress and the percent repaired was calculated as follows:

$$\% \text{ of split ends repaired} = \frac{(\text{Original \# of split ends}) - (\text{\# of split ends remaining})}{(\text{Original \# of split ends})} \times 100$$

The following results were obtained:

| Product | Original # of Split Ends | Final # of Split Ends | % Repaired |
|---|---|---|---|
| Formula 1 | 44 | 21 | 52.3 |
| Formula 2 | 42 | 27 | 35.7 |

It was thus confirmed that sodium was a preferred surfactant cation to ammonium; it was further confirmed that a shampoo of the type described in the '348 Patent can effect a reduction in the number of split ends seen in damaged hair.

Example 2

Shampoo Formulations: Addition of Necons

The Necons used in the experiments in this Example, and in Example 3, were:

Polyethyleneoxide 15-cocamine phosphate/oleate complex (Necon CPS-65),
lauryldimethylamine lactate (Necon LL),
lauryldimethylamine oleate (Necon LO),
lauryldimethylamine dimer dilinoleate (Necon DLD),
linoleamidopropyldimethylamine lactate (Necon SOLC), behenamidopropyldimethylamine behenate (Necon BAB), behenamidopropyldimethylamine dimer dilinoleate (Necon BD),
and linoleamidopropyldimethylamine dimer dilinoleate (Necon LO-80).

Except as otherwise indicated hereinafter, the materials and methods for the experiments of this Example, and of Example 3, were those disclosed above for Example 1.

The results of the experiments of Example 1, coupled with the disclosure of the '348 Patent, would suggest that in order to make a split end treatment shampoo one needs amphoterically or cationically modified guar gum along with ingredients that provide lipophilic conditioning (e.g., the silicone polyurethane of the '348 Patent), and possibly additional ingredients that cause adhesion (e.g., the betaine polyurethane surfactant of the '348 Patent). Although the Necon products do provide conditioning, and they are substantive to skin and hair, there is no evidence that they are adhesive or promote adhesion and they are not polymers. The following Formulations were prepared to test the efficacy of Necons in shampoo formulations intended to repair split ends, as listed in Table 2.

TABLE 2

| | Formulations 3, 4, 5, 6 & 7 | | | | |
|---|---|---|---|---|---|
| Ingredients | 3 % | 4 % | 5 % | 6 % | 7 % |
| Phase A | | | | | |
| Stepanol WAC | 15.00 | 15.00 | 15.00 | 15.00 | 15.00 |
| Steol CS-230 | 15.00 | 15.00 | 15.00 | 15.00 | 15.00 |
| Foamtaine CABG (35) | 15.00 | 15.00 | 15.00 | 15.00 | 15.00 |
| Acyl Glutamate CS-22 | 7.00 | 7.00 | 7.00 | 7.00 | 7.00 |
| Necon LO-80 | 2.00 | — | — | — | — |
| Necon DLD | — | 2.00 | — | — | — |
| Necon CPS-65 | — | — | 3.00 | — | — |
| Phenobact | 1.00 | 1.00 | 1.00 | 1.00 | 1.00 |
| Phase B | | | | | |
| Deionized Water | 44.75 | 44.75 | 43.75 | 46.75 | 47.00 |
| Jaguar C-13S | 0.25 | 0.25 | 0.25 | 0.25 | — |
| | 100.00 | 100.00 | 100.00 | 100.00 | 100.00 |

Two Test Runs (1 and 2) were conducted with these formulations using the procedure outlined previously for Formulations 1 and 2 modified as follows:

(1) Both 2 gram tresses were shampooed together using 2 cc's of shampoo.
(2) Rinsing was done for 30 seconds instead of one minute.
(3) The split end tresses were evaluated after air drying for 3 to 5 hrs.

The results from the first test showed:
Formul. 3—72% split end repair—13 repaired out of 18
Formul. 4—61% split end repair—11 repaired out of 18
Formul. 5—83% split end repair—15 repaired out of 18
Formul. 6—47% split end repair—9 repaired out of 19
Formul. 7—not tested An expansion and repeat of this test showed the following results:
Formul. 3—78% split end repair—32 repaired out of 41
Formul. 4—83% split end repair—35 repaired out of 42
Formul. 5—76% split end repair—32 repaired out of 42
Formul. 6—56% split end repair—24 repaired out of 43
Formul. 7—18% split end repair—7 repaired out of 40

The combined (averaged) test results are set forth in Table 3:

TABLE 3

| Product | Original # of Split Ends | Final # of Split Ends | % Reduction | Necon |
|---|---|---|---|---|
| Formul. 3 | 59 | 14 | 76.2 | LO80 |
| Formul. 4 | 60 | 14 | 76.6 | DLD |
| Formul. 5 | 60 | 13 | 78.3 | CPS65 |
| Formul. 6 | 62 | 29 | 53.2 | none |
| Formul. 7 | 40 | 33 | 17.5 | none |

These results clearly show that shampoos formulated with several of the Necon conditioning agents and cationic guar gum are effective at repairing split ends in hair. They further demonstrate that formulations containing a guar gum alone do not achieve much more than 50% split end repair.

Example 3

Shampoo Formulations: Necon Optimization

The shampoo formulations listed below in Tables 4 and 5 were prepared in accordance with the instant invention.

TABLE 4

| | Formulations 8, 9, 10, 11, 12, 13 and 14 | | | |
|---|---|---|---|---|
| INGREDIENTS | 8 | 9 | 10 | 11 |
| Steol CS 330 | 15.00 | 15.00 | 15.00 | 15.00 |
| Stepanol WAC | 15.00 | 15.00 | 15.00 | 15.00 |
| Foamtaine CAB | 15.00 | 15.00 | 15.00 | 15.00 |
| Ajinomoto CS-22 | 7.00 | 7.00 | 7.00 | 7.00 |
| Phenobact | 1.00 | 1.00 | 1.00 | 1.00 |
| Necon SOLC | 2.00 | — | — | — |
| Necon BAB | — | 2.00 | — | — |
| Necon LO | — | — | 2.00 | — |
| Necon BD | — | — | — | 2.00 |
| Jaguar C13S | 0.25 | 0.25 | 0.25 | 0.25 |
| Deionized Water | 44.65 | 44.65 | 44.65 | 44.65 |
| Citric Acid | 0.10 | 0.10 | 0.10 | 0.10 |

TABLE 5

| INGREDIENTS | 12 | 13 | 14 |
|---|---|---|---|
| Steol CS 330 | 15.00 | 15.00 | 15.00 |
| Stepanol WAC | 15.00 | 15.00 | 15.00 |
| Foamtaine CAB | 15.00 | 15.00 | 15.00 |
| Ajinomoto CS-22 | 7.00 | 7.00 | 7.00 |
| Phenobact | 1.00 | 1.00 | 1.00 |
| Necon LO 80 | 2.00 | — | — |
| Necon LL | — | 2.00 | — |

TABLE 5-continued

| INGREDIENTS | 12 | 13 | 14 |
|---|---|---|---|
| Necon DLD | — | — | 2.00 |
| Jaguar C13S | 0.25 | 0.25 | 0.25 |
| Deionized Water | 44.65 | 44.65 | 44.65 |
| Citric Acid | 0.10 | 0.10 | 0.10 |

Five tress combinations were grouped together for testing with each of the shampoos described in Tables 4 and 5. Thus, for each shampoo, about 100 split end repair evaluations were made. The tresses were shampooed as seven groups with five tresses in each group using 1 cc of shampoo per tress (5 cc's per group). The tress group was shampooed for 1 minute, rinsed for 30 seconds under running warm (40° C.) tap water and the process was repeated. The tress group was then separated into individual tresses; the split end tress was removed and hung to dry separately for 3 hours and was then evaluated.

The results are listed in Table 6. Table 6 charts the percent split end repair for each of the 5 split end tresses in the seven test groups. An average percent split end repair is calculated for each group and, based upon the variation in percent split end repair between each tress in the group, a standard deviation and a 95% confidence interval are calculated. The data in Table 6 is presented graphically in FIG. 1, which illustrates the mean percent split end repair for each treatment along with the added and subtracted 95% confidence interval (CI) values. Thus, if the mean for one treatment is less than the mean for another treatment minus its CI, then there is a 95% confidence level that a significant difference exists between the two means. As can be seen from FIG. 1 and Table 6, the mean for treatment LL is lower than the mean minus CI values for treatments LO, BAB and DLD. In addition, the means for treatments LL and BD are lower than the mean minus CI values for treatment DLD.

TABLE 6

Percent Split End Repair Effective by Shampoos Containing Necons

| Tress # | Necon LL | Necon BAB | Necon LO 80 | Necon DLD | Necon LO | Necon BD | Necon SOLC |
|---|---|---|---|---|---|---|---|
| 1 | 75 | 81 | 82 | 62 | 76 | 48 | 85 |
| 2 | 58 | 90 | 65 | 81 | 71 | 75 | 62 |
| 3 | 63 | 65 | 81 | 90 | 89 | 65 | 68 |
| 4 | 75 | 68 | 61 | 76 | 76 | 90 | 64 |
| 6 | 68 | 81 | 70 | 85 | 65 | 68 | 74 |
| Average | 67.8 | 77 | 71.8 | 78.8 | 75.4 | 69.2 | 70.6 |
| Std. Dev. | 7.463243 | 10.3198837 | 9.418067742 | 10.7098086 | 8.848729 | 15.28725 | 9.26282894 |
| Conf. int 95% (C.I.) | 6.541691 | 9.0455973 | 8.255136441 | 9.38737473 | 7.756099 | 13.3996 | 8.1190633 |
| Ave. PLUS C.I. | 74.34169 | 86.0455973 | 80.055136356 | 88.1873747 | 83.1561 | 82.5996 | 78.7190663 |
| Ave. MINUS C.I. | 61.25831 | 67.9544027 | 63.54486356 | 69.4126253 | 67.6439 | 55.8004 | 62.4809337 |
|  | A | B | C | D | E | F | G |

The following conclusions were drawn from these experiments: (1) treatment with the Necon LL containing shampoo produces less split end repair of hair (at the 95% confidence level) than that seen with shampoos containing Necon BAB or Necon DLD and slightly less than Necon LO; (2) treatment with the Necon LL or Necon BD containing shampoo produces less split end repair of hair (at the 95% confidence level) than that seen with the shampoo containing Necon DLD; (3) treatment with the Necon LO, Necon BAB or Necon DLD-containing shampoos produces greater split end repair of hair (at the 95% confidence level) than that seen with the shampoo containing Necon LL;. (4) treatment with the Necon DLD containing shampoo produces greater split end repair of hair (at the 95% confidence level) than that seen with the shampoo containing either Necon SOLC or Necon LL; and (5) all Necon-containing shampoo formulations tested achieve acceptable split end repair levels.

What is claimed is:

1. A method for repairing split ends of hair comprising contacting the hair with a formulation comprising:

(a) an amphoteric or cationic guar gum; and
   (b) a fatty dialkyl amine salt according to the formula:

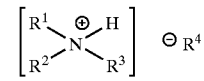

where $R^1$ is a $C_8$ to $C_{40}$ straight or branch-chained, saturated or unsaturated hydrocarbon group or a fatty amido group according to the formula:

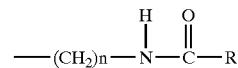

where R is a $C_8$ to $C_{40}$ straight or branch-chained, saturated or unsaturated hydrocarbon group
   n is from 1 to 5;
   $R^2$ and $R^3$ are independently methyl, ethyl or propyl groups; and
   $R^4$ is a $C_2$ to $C_{40}$ acid anionic residue or diacid dianionic residue
   wherein the formulation only contains natural or synthetic gums.

2. The method of claim 1, wherein the fatty dialkyl amine salt is made from either monofunctional amines or acids or from dimer acids.

3. The method of claim 2, wherein the formulation is a shampoo, an emulsion, a gel, or a rinse.

4. The method of claim 1, wherein said formulation is a shampoo comprising:

(a) 0.05% to 5.0% by weight of said fatty dialkyl amine salt;
   (b) 0.05% to 5.0% by weight of said amphoteric or cationic guar gum; and
   (c) 20% to 90% by weight of water.

5. The method of claim 4, wherein the formulation further comprises one or more of the following: a surfactant, a conditioning agent, an emollient, a humectant, an emulsifier, an opacifying agent, a thickening agent, a foam stabilizer, a viscosity builder, a preservative, a sequestrate, an antioxidant, an antidandruff agent, a chelating agent, a suspending agent, a pH control agent, a protein, a fragrance, a sunscreen, or a botanical extract.

6. The method of claim 4, wherein the formulation comprises from about 0.10% to about 0.50% by weight of guar hydroxypropyl trimonium chloride and from about 1% to about 5% by weight of lauryldimethylamine dimer dilinoleate.

7. The method of claim 4, wherein the formulation comprises:
   (a) a surfactant blend including the anionic surfactant sodium N-cocoyl 1-glutamate;
   (b) a microbial preservative;
   (c) around 0.20% to 0.30% by weight of guarhydroxypropyl trimonium chloride;
   (d) around 1.0% to 3.0% by weight of a dialkylamine salt selected from the group consisting of polyethyleneoxide 15-cocamine phosphate/oleate complex, lauryldimethylamine lactate, lauryldimethylamine oleate, lauryldimethylamine dimer dilinoleate, linoleamidopropyldimethylamine lactate, behenamidopropyldimethylamine behenate, behenamidopropyldimethylamine dimer dilinoleate, and linoleamidopropyldimethylamine dimer dilinoleate; and
   (e) around 40% to 60% by weight of water.

* * * * *